United States Patent
Rangaswamy et al.

(10) Patent No.: US 9,725,745 B2
(45) Date of Patent: Aug. 8, 2017

(54) PROCESS FOR BIODIESEL PRODUCTION FROM A YEAST STRAIN

(75) Inventors: Vidhya Rangaswamy, Navi Mumbai (IN); Saurabh Saran, Navi Mumbai (IN); Mithra Kannabiran, Navi Mumbai (IN); Meikandhan Thiru, Navi Mumbai (IN); Santosh Sankh, Navi Mumbai (IN)

(73) Assignee: RELIANCE LIFE SCIENCES PVT. LTD., Maharashtra (IN)

( * ) Notice: Subject to any disclaimer, the term of this patent is extended or adjusted under 35 U.S.C. 154(b) by 711 days.

(21) Appl. No.: 13/504,605

(22) PCT Filed: Oct. 29, 2010

(86) PCT No.: PCT/IN2010/000712
§ 371 (c)(1),
(2), (4) Date: Aug. 9, 2012

(87) PCT Pub. No.: WO2011/051977
PCT Pub. Date: May 5, 2011

(65) Prior Publication Data
US 2012/0317877 A1 Dec. 20, 2012

(30) Foreign Application Priority Data
Oct. 29, 2009 (IN) .......... 2514/MUM/2009

(51) Int. Cl.
*C10L 1/18* (2006.01)
*C12P 7/64* (2006.01)
*C12R 1/84* (2006.01)

(52) U.S. Cl.
CPC ............ *C12P 7/649* (2013.01); *C12P 7/6463* (2013.01); *C12R 1/84* (2013.01);
(Continued)

(58) Field of Classification Search
CPC .......... C10G 2300/1011; C12P 7/6463; C12P 7/649; C12R 1/84; C10L 1/026; C11C 3/003; Y02E 50/13; Y02E 50/17
(Continued)

(56) References Cited

U.S. PATENT DOCUMENTS 3,909,352 A * 9/1975 Akiyama ............... C12N 1/16
435/248
5,756,472 A * 5/1998 Liesch .................. C07H 15/24
435/254.1
(Continued)

FOREIGN PATENT DOCUMENTS

WO WO-2009/009391 A2 1/2009

OTHER PUBLICATIONS

Ratledge. "Microogranisms for Lipids". 1991. Acta Biotechnology. pp. 429-438.*
(Continued)

*Primary Examiner* — Latosha Hines
(74) *Attorney, Agent, or Firm* — Westman, Champlin & Koehler, P.A.

(57) ABSTRACT

Disclosed herein are methods and compositions related to the production and extraction of oils and biodiesel from oleaginous yeast, such as a new yeast isolate of the genus *Pichia*. Also disclosed herein are methods for providing fermentation conditions for the production of yeast in high density using inexpensive raw materials including crude glycerol and corn steep liquor.

18 Claims, 8 Drawing Sheets

(52) U.S. Cl.
 CPC ....... *C10G 2300/1011* (2013.01); *Y02E 50/13* (2013.01); *Y02P 30/20* (2015.11)
(58) Field of Classification Search
 USPC .................. 44/385, 401; 435/134, 255.5
 See application file for complete search history.

(56) References Cited

U.S. PATENT DOCUMENTS

2010/0234458 A1* 9/2010 Dubreucq ............... C10L 1/026
 514/529
2011/0044972 A1* 2/2011 Fieldhouse ............... A23L 1/30
 424/115

OTHER PUBLICATIONS

Ratledge. "Microogranisms for Lipids". 1991. Acta Biotechnology, pp. 429-438.*
Ratledge, C., "Microorganisms for Lipids", Acta Biotechnol. 11, 1991, 5, pp. 429-438.
Ykema, Adrie et al., "Optimizatipn of lipid production in the oleaginous yeast *Apiotrichum curvatum* in wheypermeate", Appl Microbiol Biotechnol, 1988, 29:211-218.
Palmieri, Luigi, "Identification by bacterial expression and functional reconstitution of the yeast genomic sequence encoding the mitochondrial dicarboxylate carrier protein", FEBS Letters 399, 1996, pp. 299-302.
Ykema, Adrie, "Lipid Production in the Oleaginous Yeast *Apiotrichum curvatum*", Free University Amsterdam, The Netherlands, Sep. 12, 1989.
Davies, R.J., "Yeast Oil from Cheese Whey, Process Development", Moreton RS (ed) Single cell oil, Longman, London, 1988, pp. 99-145.
Li, Q, "Use Food Industry Waste to Produce Microbial Oil", Science and Technology of Food Industry, 1997, 6:65-69.
Ma, Y.L., "Microbial Oils and Its Research Advance", Chinese Journal Bioprocess, Engineering, Nov. 2006, 4(4):7-11.
Boulton, Christopher et al., "Regulatory Studies on Citrate Synthase in Candida 107, an Oleaginous Yeast", Journal of General Microbiology (1980), 121, 441-447.
Wan, Xia et al., "Production of Gamma-Linolenic Acid in Pichia pastoris by Expression of a Delta-6 Desaturase Gene from *Cunninghamella echinulata*", J. Microbiol Biotechnol, (2009), 19(10), 1098-1102.
Dai, Chuan-chao et al., "Biodiesel generation from oleaginous yeast Rhodotorula glutinis with xylose assimilating capacity", African Journal of Biotechnology, vol. 6 (18), pp. 2130-2134, Sep. 19, 2007.
Li, Qiang et al., "Perspectives of microbial oils for biodiesel production", Appl Microbiol Biotechnol (2008) 80: 749-756.
Daniel, Heide-Marie, et al., "Yeast diversity of Ghanaian cocoa bean heap fermentations", FEMS Yeast Res, 9 (2009) 774-783.
Pan, Li-Xia et al., "Isolation of the Oleaginuos Yeasts from the Soil and Studies of Their Lipid-Producing Capacities", Food Technol. Biotechnol, 47 (2) 215-220 (2009).
Evans, Christopher T. et al., "Effect of Nitrogen Source on Lipid Accumulation in Oleaginous Yeasts", Journal of General Microbiology (1984), 130, 1693-1704.
Cupp, Jill R. et al, "Cloning and Characterization of the Gene Encoding the IDH1 Subunit of $NAD^+$-dependent Isocitrate Dehydrogenase from *Saccharomyces cervisiae**", The Journal of Biological Chemistry, vol. 267, No. 23, Aug. 15, 1992, 16417-16423.
Folch, Jordi et al., "A Simple Method for the Isolation and Purification of Total Lipides From Animal Tissues*", 1957, J. Biol Chem. 226: 497-509.
Meesters, P.A.E.P., et al., "High-cell-density cultivation of the lipid accumulating yeast *Cryptococcus curvatus* using glycerol as a carbon source", Appl Microbiol Biotechnol (1996) 45: 575-579.
van Voorst, Frank, "International Search Report", for PCT/IN2010/000712 as mailed May 27, 2011, 4 pages.

* cited by examiner

PROCESS FOR BIODIESEL PRODUCTION FROM A YEAST STRAIN

CROSS-REFERENCE TO RELATED PATENT APPLICATIONS

The present application claims benefit of the filing date of Indian Provisional Patent 2514/MUM/2009 filed on 29 Oct. 2009, which is entirely incorporated herein by reference.

TECHNICAL FIELD

The present disclosure relates to oleaginous yeast, including *Pichia kudriavzevii*, a species of the genus *Pichia*, as well as a novel *Pichia kudriavzevii* yeast strain deposited under Accession No. MTCC 5493, and to the production of oil and biodiesel from oleaginous yeast.

BACKGROUND

Biodiesel is an environmentally benign solution for global warming, the energy crisis and depleted fossil fuel supplies. Today, biodiesel (e.g., fatty acid methyl esters, "FAMEs"), is the name given to clean burning alternative fuels, produced from biological, renewable resources that are biodegradable and non-toxic. Biodiesel can be used directly or can be blended at any level with petroleum products, such as petroleum diesel.

Biofuels have clear benefits in addressing environmental concerns related to greenhouse gases, and offer new income to farmers. However, traditional oil-rich crops are limited by land availability, as well as environmental and social issues regarding the use of feed and food crops for fuel. An alternative way to produce biodiesel in a green and sustainable manner without competing with food crops is to use microbes. There are a few microorganisms in nature that have the inherent ability to accumulate or store oil/lipid up to 60% of their dry weight when grown under nitrogen-limited conditions. These lipids usually consist of 80%-90% triacylglycerols with a fatty acid composition similar to many plant seed oils (Ratledge, C., Evans, C. T. (1984) Influence of nitrogen metabolism on lipid accumulation in oleaginous yeasts. *J. Gen. Microbiol.* 130:1693-704. Ykema A, Verbree E C, Kater M M, Smit H (1988) Optimization of lipid production in the oleaginous yeast *Apiotrichum curvatum* in whey permeate. Appl Microbiol Biotechnol 29:211-218). These organisms are called oleaginous microorganisms. Microbial oils, also called single cell oils, are produced by some oleaginous microorganisms, such as yeast, fungi, bacteria and microalgae (Ma, Y. L. (2006) Microbial oils and its research advance. Chin. *J. Bioprocess. Eng.* 4(4):7-11.). It has been demonstrated that such microbial oils can be used as feedstock for biodiesel production. In comparison to other vegetable oils and animal fats, the production of microbial oil has many advantages: microbes have a short life cycle as compared to plants so the time to harvest is shorter, there is less labor required, microbial oil production is less affected by venue, season and climate, and scale-up is easier (Li, Q., Wang, M. Y. (1997) Use food industry waste to produce microbial oil. Science and Technology of Food Industry 6:65-69.). Therefore, microbial oil has a tremendous potential to become one of the major oil feedstocks for biodiesel production in the future. Although not a new concept, work in this area has been very limited (Li, Qiang., Wei, Du., Dehua, Liu. (2008) Perspectives of microbial oils for biodiesel production. *Appl. Microbiol. Biotechnol.* 80:749-756.).

Microbial cells studied to date for use in biodiesel production include bacteria, yeast and fungi. Preferred fungus genera include *Mortierella, Phycomyces, Entomophthora, Pythium, Thraustochytrium, Blakeslea, Rhizomucor* and *Aspergillus*. Exemplary bacteria that have been studied include those of the genus *Propionibacterium*. Studied algae include dinoflagellate and/or belong to the genus *Crypthecodinium, Porphyridium* or *Nitschia*, for example *Crypthecodinium cohnii*.

Yeasts such as *Yarrowia, Candida, Rhodotorula, Rhodosporidium, Cryptococcus, Trichosporon* and *Lipomyces* have been studied for their microbial oil properties and among these oleaginous yeasts, *Cryptococcus curvatus* has attracted attention because it can accumulate large amounts of oil, up to 60% of the cell's dry weight (Ratledge, C. (1991). Microorganisms for lipids. *Acta. Biotechnol.* 11:429-438), utilizing cheap carbon sources like whey permeate (Ykema, A. (1989) Lipid production in the oleaginous yeast *Apiotrichum curvatum*. PhD thesis. Free University Amsterdam, The Netherlands.) and other carbohydrate-rich agricultural or food processing wastes. The yeast oil produced by *C. curvatus* resembles plant seed oils like palm oil (Davies, R. J. (1988) Yeast oil from cheese whey; process development. In: Moreton R S (ed) Single cell oil. Longman, London, pp 99-145.). Yeasts of the genus *Pichia* and *Saccharomyces*, for example *Pichia ciferrii*, have also been studied.

Currently, the production of yeast oil is more expensive than the production of vegetable oil. Therefore, single-cell oil fermentation will be economically feasible when a particular oil can be produced with high added value. Accordingly, previous approaches have used process engineering to yield a higher lipid production rate, a higher cellular lipid content, and higher biomass production, all geared to make the process more economically feasible. Different cultivation modes, including fed-batch and continuous fermentations, have been reported to increase the cell density of oleaginous microbes in culture. However, none of the prior art focuses on the efficient extraction of oil from fermentation media.

SUMMARY OF INVENTION

Disclosed herein is a novel, isolated strain of oleaginous yeast known as *Pichia kudriavzevii* that has been deposited under Microbial Type Culture Collection ("MTCC") Accession No. 5493. Also disclosed herein are certain methods of fermenting oleaginous yeast such as *Pichia kudriavzevii*, methods of fermenting oleaginous yeast such as *Pichia kudriavzevii*, methods of extracting the oil produced by oleaginous yeast such as *Pichia kudriavzevii*, and methods of producing biodiesel from oleaginous yeasts such as *Pichia kudriavzevii*. In some embodiments, the methods use inexpensive and economical components and processes.

Accordingly, disclosed herein is an isolated yeast cell of *Pichia kudriavzevii*, MTCC Deposit No. 5493. In some embodiments, the isolated yeast cell is able to accumulate at least 50%, or about 50%, of its weight as oil under oil production conditions. In some embodiments, the isolated yeast cells is in a culture medium. In some embodiments, the culture medium includes crude glycerol, corn steep liquor, and yeast autolysate.

Also disclosed herein is a *Pichia kudriavzevii* yeast strain deposited under Accession No. MTCC 5493. Also disclosed herein is a biologically pure culture of *Pichia kudriavzevii*, MTCC 5493. Also disclosed herein is a microbial composition including an isolated yeast cell of *Pichia kudriavzevii*, MTCC 5493. Also disclosed herein are compositions comprising oil produced by isolated yeast cells. In some embodiments, the isolated yeast cell is *Pichia kudriavzevii*, MTCC Deposit No. 5493. In some embodiments, the oil includes at least about 10% palmitic acid, at least about 8% palmitoleic acid, at least about 1% stearic acid, at least about 41% oleic acid, at least about 15% linoleic acid, and at least about 6% linolenic acid. In some embodiments, the extracted oil has been subject to transesterification.

Also disclosed herein are compositions including, an isolated yeast cell and a culture medium. In some embodiments, the culture medium includes crude glycerol at about 1% w/v, corn steep liquor at about 2% w/v, yeast autolysate at about 0.5% w/v, wherein the composition has a pH of about 5.5. In some embodiments, the yeast cells include *Pichia kudriavzevii*, MTCC Deposit No. 5493.

Also disclosed herein are methods for culturing yeast cells to induce oil production by the cells. In some embodiments, the methods include providing a culture medium that includes crude glycerol at about 1% w/v, corn steep liquor at about 2% w/v, *cryptococcus* yeast autolysate at about 0.5% w/v, wherein the culture medium has a pH of about 5.5; and fermenting the yeast cells in the culture medium using fed batch fermentation at about 28° C. for at least about 100 hours. In some embodiments the yeast cells include *Pichia kudriavzevii*, MTCC Deposit No. 5493. In some embodiments, the fermentation runs for at least about 110 hours. In some embodiments, the fed batch fermentation involves adding glycerol during the fermentation. In some embodiments, the added glycerol includes crude glycerol. In some embodiments, glycerol is added to the culture medium when the glycerol concentration of the fermentation is below about 8 g/L. In other embodiments, fermentation continues until the OD of the yeast cells is between about 110 and 150. In some embodiments, the fermentation results in an oil yield of at least about 14% on a dry weight basis. In other embodiments, the fermentation results in an oil yield of at least about 20% on a dry weight basis. In still other embodiments, the fermented cell biomass after fermentation is at least about 30 g/L on a dry weight basis. In some embodiments the yeast cells include *Pichia kudriavzevii*, MTCC Deposit No. 5493.

Also disclosed herein are methods for producing oil that includes fatty acid methyl esters. In some embodiments, the methods include culturing the isolated yeast cell oil production conditions, and; extracting the oil from the cultured yeast cells. In some embodiments, the extracted oil is transesterified. In some embodiments, culturing under oil production conditions includes providing a culture medium including crude glycerol at about 1% w/v, corn steep liquor at about 2% w/v, *cryptococcus* yeast autolysate at about 0.5% w/v, wherein the culture medium has a pH of about 5.5; and fermenting the yeast cell in the culture medium using fed batch fermentation at about 28° C. for at least about 100 hours. In some embodiments the yeast cells include *Pichia kudriavzevii*, MTCC Deposit No. 5493.

Also disclosed herein are methods for producing biodiesel including fatty acid methyl esters. In some embodiments, the methods include culturing yeast cells, for example, *Pichia kudriavzevii*, MTCC Deposit No. 5493 cells, under oil production conditions; extracting oil from the cultured yeast cells, and; transesterifying the extracted oil.

Also disclosed herein are methods for producing biodiesel which includes fatty acid methyl esters. In some embodiments, the methods comprise culturing yeast cells comprising *Pichia kudriavzevii*, MTCC Deposit No. 5493, under oil production conditions, and; extracting fatty acid methyl esters by direct transesterification. In other embodiments, the methods include culturing yeast cells comprising *Pichia kudriavzevii*, MTCC Deposit No. 5493, under oil production conditions, and; isolating fatty acid methyl esters from the cultured yeast cells. In still other embodiments, the methods include culturing the isolated yeast cells, such as *Pichia kudriavzevii*, MTCC Deposit No. 5493, under oil production conditions, and; isolating fatty acid methyl esters from the cultured yeast cells.

Accordingly, disclosed herein is an isolated yeast cell of *Pichia kudriavzevii*, identified under MTCC Accession No. 5493. In some embodiments, the isolated yeast cell is able to accumulate about 50% of its weight as oil under oil production conditions. In some embodiments, the isolated yeast cells is in a culture medium. In some embodiments, the culture medium includes crude glycerol, corn steep liquor, and yeast autolysate.

Also disclosed herein are isolated yeast cells of a *Pichia kudriavzevii* strain, as deposited under Accession No. MTCC 5493. Also disclosed herein is a biologically pure culture of *Pichia kudriavzevii*, MTCC 5493. Also disclosed herein is a microbial composition including an isolated yeast cell of *Pichia kudriavzevii*, MTCC 5493. Also disclosed herein are compositions including oil produced by isolated yeast cells; in some embodiments, the isolated yeast cell is *Pichia kudriavzevii*, MTCC Deposit No. 5493. In some embodiments, the oil includes at least about 10% palmitic acid, at least about 8% palmitoleic acid, at least about 1% stearic acid, at least about 41% oleic acid, at least about 15% linoleic acid, and at least about 6% linolenic acid. In some embodiments, the extracted oil has been subject to transesterification.

Also disclosed herein are compositions including an isolated yeast cell and a culture medium. In some embodiments, the culture medium includes crude glycerol at about 1% w/v, corn steep liquor at about 2% w/v, yeast autolysate at about 0.5% w/v, wherein the composition has a pH of about 5.5. In some embodiments, the yeast cells include *Pichia kudriavzevii*, MTCC Deposit No. 5493.

Also disclosed herein are methods for culturing yeast cells to induce oil production by the cells. In some embodiments, the methods include providing a culture medium which includes crude glycerol at about 1% w/v, corn steep liquor at about 2% w/v, *cryptococcus* yeast autolysate at about 0.5% w/v, wherein the culture medium has a pH of about 5.5; and fermenting the yeast cells in the culture medium using fed batch fermentation at about 28° C. for at least about 100 hours. In some embodiments the yeast cells include *Pichia kudriavzevii*, MTCC Deposit No. 5493. In some embodiments, the fermentation runs for at least about 110 hours. In some embodiments, the fed batch fermentation involves adding glycerol during the fermentation. In some embodiments, the added glycerol includes crude glycerol. In some embodiments, glycerol is added to the culture medium when the glycerol concentration of the fermentation is below about 8 g/L. In other embodiments, fermentation continues until the OD of the yeast cells is between about 110 and 150. In some embodiments, the fermentation results in an oil yield of at least about 14% on a dry weight basis. In other embodiments, the fermentation results in an oil yield of at least about 20% on a dry weight basis. In still other embodiments, the fermented cell biomass after fermentation is at least about 30 g/L on a dry weight basis. In some embodiments the yeast cells include *Pichia kudriavzevii*, MTCC Deposit No. 5493.

Also disclosed herein are methods for producing oil that comprise fatty acid methyl esters. In some embodiments, the methods include culturing the isolated yeast cell oil production conditions, and extracting the oil from the cultured yeast cells. In some embodiments, the extracted oil is transesterified. In some embodiments, culturing under oil production conditions includes providing a culture medium including crude glycerol at about 1% w/v, corn steep liquor at about 2% w/v, *cryptococcus* yeast autolysate at about 0.5% w/v, wherein the culture medium has a pH of about 5.5; and fermenting the yeast cell in the culture medium using fed batch fermentation at about 28° C. for at least about 100 hours. In some embodiments the yeast cells include *Pichia kudriavzevii*, MTCC Deposit No. 5493.

Also disclosed herein are methods for producing biodiesel including fatty acid methyl esters. In some embodiments, the methods include culturing yeast cells, for example, *Pichia kudriavzevii*, MTCC Deposit No. 5493 cells, under oil production conditions, extracting oil from the cultured yeast cells, and transesterifying the extracted oil.

Also disclosed herein, are methods for producing biodiesel that comprise fatty acid methyl esters. In some embodiments, the methods comprise culturing yeast cells comprising *Pichia kudriavzevii*, MTCC Deposit No. 5493, under oil production conditions, and extracting fatty acid methyl esters by direct transesterification. In other embodiments, the methods include culturing yeast cells comprising *Pichia kudriavzevii*, MTCC Deposit No. 5493, under oil production conditions, and isolating fatty acid methyl esters from the cultured yeast cells. In still other embodiments, the methods include culturing the isolated yeast cells, such as *Pichia kudriavzevii*, MTCC Deposit No. 5493, under oil production conditions, and isolating fatty acid methyl esters from the cultured yeast cells.

BRIEF DESCRIPTION OF DRAWINGS

The following drawings form part of the present specification and are included to further demonstrate certain aspects of the present disclosure which may be better understood by reference to one or more of the drawings in combination with the detailed description.

DETAILED DESCRIPTION

I. Definitions

Figure 1:
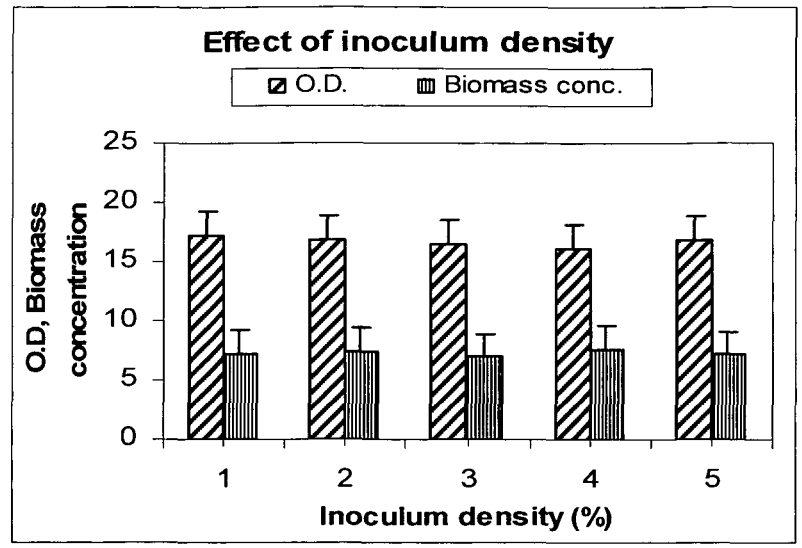
FIG. 1 shows the effect of inoculum density on biomass production for *Pichia kudriavzevii* (deposited under MTCC Accession No. 5493).

The term "*Pichia kudriavzevii*" as used herein refers a species of the yeast genus *Pichia*. One example is a new yeast strain deposited under MTCC Accession No. 5493.

The term "biodiesel" means a diesel fuel comprising long-chain alkyl (methyl, propyl or ethyl) esters. A biodiesel may comprise fatty acid methyl esters ("FAMEs") of oil isolated from yeast, including chemical variants or modifications of the FAMEs.

The term "oil" as used herein, with respect to oil isolated from or produced by yeast, refers to lipids (such as fatty acid methyl esters) produced in yeast, or lipids or total lipid content isolated from yeast.

The term "oil production conditions" as used herein refers to growth or fermentation conditions in which yeast will produce oil. Such conditions may include a medium with an excess of carbon and limited amounts of other nutrients, specifically nitrogen. In some embodiments, "oil production conditions" are realized when the ratio of carbon source to nitrogen source in the growth medium is about 40-50. In some embodiments, "oil production conditions" are realized when the tricarboxylic acid cycle is repressed, the metabolic pathway is altered, protein synthesis ceases and the lipid accumulation process is activated. In some embodiments, "oil production conditions" are realized when NAD-IDH activity is decreased or absent in the oleaginous yeast strain as compared to the same yeast strain under control conditions, and the oleaginous yeast strain can no longer utilize acetic acid as a carbon source, but can utilize glycerol or lactic acid as a carbon source.

As used herein, the term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 1.0% of the particular term, including plus or minus 5%, 1%, 0.1%, 0.01%, or refer generally to a standard deviation seen when using standard procedures for measurement.

As used herein, the term "transesterification" or "transesterifying" refers to the process of exchanging the organic group R" of an ester with the organic group R' of an alcohol. A schematic reaction is shown below.

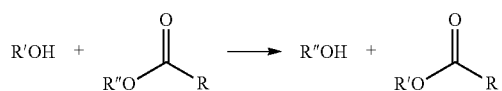

As used herein, the term "culturing" means the process by which cells (e.g., yeast cells) are grown under human controlled conditions. In some embodiments, culturing includes fermenting.

As used herein, the term "culture medium" or "growth medium" or "fermentation medium" means a liquid or gel designed to support the growth of microorganisms or cells, for example, yeast cells.

As used herein, the term "yeast cell biomass" refers to yeast cells that are produced by fermentation or by other culturing means. In some embodiments, the yeast cell biomass has been collected by centrifugation and separated to some degree from the culture or fermentation medium. "Fermented yeast cell biomass" refers to yeast cells that are produced by fermentation.

As used herein, the term "dry weight basis" means the mass of a composition when at least some of the liquid portion has been removed. For example, to determine the dry weight of fermented yeast cell biomass, one ml of culture is centrifuged at 10,000 rpm for 10 minutes. The biomass pellet is washed twice with distilled water and dried at 40° C. to constant mass (usually 24 h). In this example, the biomass is determined gravimetrically, and is provided in units of gram per milliliter, grams per liter, etc.

As used herein the term "oil yield on a dry weight basis" means the amount of oil produced by a unit of yeast cell biomass measured on a dry weight bases. For example, if the yeast cell biomass on a dry weight basis is 32.8 g/L, and 7 g of oil are extracted from this biomass, the oil yield is 21% on a dry weight basis.

As used herein, the term "isolated," when used in conjunction with a yeast strain, refers to a yeast cell that is substantially or essentially free from non-yeast components that normally accompany or interact with the yeast cell as found in its naturally occurring environment. Thus, an isolated yeast cell is one that is no longer in its natural environment, and is, for example, growing or preserved in culture, for example in a laboratory.

II. Isolation of a Novel Oleaginous Yeast Strain

Yeasts isolated from various rotten fruit samples were screened for their ability to produce oil. Eight different rotten fruits samples (mango, guava, orange, pomegranate, grapes, banana, papaya and chikku) were collected from the Ghansoli fruit market, Navi Mumbai, India. Skins of the fruits were peeled and were added to 100 ml of glucose-enriched medium containing (in g/L): glucose 20, peptone 5, yeast extract 5, malt extract 3, $KH_2PO_4$ 1 and $MgSO_4.7H_2O$ 0.5, in a 250-mL Erlenmeyer flask. The samples were incubated in an incubator shaker at 28° C. for 48 hours ("h") at 200 revolutions per minute ("rpm"), to enrich for yeast.

The above enriched yeast cultures were then subjected to serial 10-fold dilutions and 0.1 ml aliquots from dilutions ranging from $10^{-6}$ to $10^{-12}$ were spread onto MGYP agar (1% glucose, 0.5% peptone, 0.5% yeast extract, 0.3% malt extract, 2% agar, and 5 ml of streptomycin solution). The plates were incubated at 28° C. for 72 h, and isolated yeast colonies were further screened for their lipid-producing ability by a solvent extraction method (Folch, J., M. Lees, and G. H. Sloane Stanley, (1957) *J. Biol. Chem.* 226: 497.) elaborated in example 13.

The isolated yeast identified as having potential for oil production was then sent to IMTECH (Institute of Microbial Technology, Chandigarh, India) for identification on the basis of sequencing the D1/D2 domain of the 26S ribosomal RNA gene. The yeast strain was found to be a novel subspecies of *Pichia kudriavzevii*.

This isolated yeast strain was deposited on Oct. 12, 2009, as deposition number MTCC 5493 in the International patent organism depository IMTECH (Institute of Microbial Technology, Chandigarh, India) for patent purposes, under the Budapest Treaty.

The novel *Pichia kudriavzevii* yeast strain may be cultured in a medium typically used for culturing yeast. The nutritive requirements may include nitrogen sources such as peptone, tryptone, yeast extract, beef extract, corn steep liquor, ammonium chloride, sodium nitrate and ammonium sulphate, and carbon sources such as glucose, galactose, starch, arabinose, glycerol, mannitol, sucrose and fructose.

Culturing may be performed under a range of conditions that do not adversely affect growth, or under condition to obtain the growth rate or growth pattern desired (e.g., under oil production conditions). Various physical and chemical parameters were evaluated for maximum growth and oil production, such as pH, inoculation density, and inoculums age. In addition, different carbon and nitrogen sources (organic and inorganic) were examined as nutritional parameters. By way of example but not by way of limitation, cultures may be grown under aerobic conditions, within a pH range of from about 5.0 to about 7.0, with an inoculum density of 1-5% and an inoculum age of 6 to 24 hours.

The present invention also provides processes for biofuel production by extraction and transesterification of the oil accumulated by an isolated yeast strain.

III. Embodiments

In some embodiments, compositions are provided that include a novel *Pichia* strain of the species *Pichia kudriavzevii* (*P. kudriavzevii*) having MTCC Accession No. 5493. In some embodiments, compositions include an isolated *P. kudriavzevii* cell wherein the cell is able to accumulate at least 50%, such as about 50%, of its weight as oil under oil production conditions. In some embodiments, the isolated *P. kudriavzevii* cell is in a culture medium that includes a nitrogen source, a carbon source and brewer's yeast or a yeast autolysate.

In some embodiments, methods are provided for screening and isolating new strains of yeast capable of accumulating oil (e.g., oleaginous yeasts). For example, in some embodiments, samples that may contain oleaginous yeasts are cultured under conditions to enrich for yeast. In some embodiments, such conditions include a glucose-enriched medium. In one exemplary embodiment, such a medium contains: 20 g/L glucose, 5 g/L peptone, 5 g/L yeast extract, 3 g/L malt extract, 1 g/L $KH_2PO_4$ and 0.5 g/L $MgSO_4.7H_2O$. In some embodiments, samples of the enriched cultures are plated such that individual colonies can be evaluated for lipid producing ability. In some embodiments, individual colonies are selected and tested (e.g., by a solvent extraction method) for their lipid producing ability.

In some embodiments, method is provided to maximize growth, conditions for oleaginous yeasts. In some embodiments, growth conditions are directed to the fermentation of oleaginous yeasts for the production and extraction of oil produced by the yeast, and/or for the manufacture of biodiesel using oil produced by the yeast. Thus, in some embodiments, growth conditions are also "oil producing conditions." In some embodiments, growth conditions or oil producing conditions are determined by evaluating one or more of the following parameters: 1) biomass of the fermented yeast; 2) optical density ("O.D.") of the fermented yeast; 3) cost per unit of the fermented yeast biomass; 4) cost per unit of the oil extracted from fermented yeast; and 5) cost per unit of biodiesel manufactured from oil produced by the yeast. In some embodiments, growth conditions (oil producing conditions) are provided for *P. kudriavzevii*, such that one or more of a desired biomass of fermented *P. kudriavzevii*, optical density ("O.D.") of the fermented *P. kudriavzevii*; cost per unit of the fermented *P. kudriavzevii* biomass; cost per unit of the oil extracted from fermented *P. kudriavzevii*; and cost per unit of biodiesel manufactured from oil produced by *P. kudriavzevii* is achieved.

In some embodiments, methods are provided for maximizing growth conditions (oil producing conditions) for oleaginous yeasts by providing certain nutritional and physiological parameters. In some embodiments, such parameters resulted in improved yields of one or more of yeast biomass, oil production, cost of a unit of fermented biomass, cost of a unit of oil produced by the fermented yeast, or cost of a unit of biodiesel manufactured from oil produced by the yeast. By way of example and not by way of limitation, physiological and nutritional parameters include inoculum age, inoculum density and pH of the fermentation medium, carbon source, carbon source concentration, nitrogen source, nitrogen source concentration, and the mode of fermentation, such as batch or fed batch fermentation.

In some embodiments, methods are provided for maximizing growth conditions (oil producing conditions) for oleaginous yeast by providing certain nutritional and physiological parameters and economizing the production of yeast biomass, oil and/or biodiesel. Thus, in some embodiments, inexpensive raw materials are used in the growth and fermentation media to maximize growth conditions (and oil production conditions). By way of example, but not by way of limitation, inexpensive raw materials include corn steep liquor (CSL), crude glycerol and de-oiled yeast autolysate, for example de-oiled *Cryptococcus* yeast autolysate. In some embodiments, medium for growth of oleaginous yeast includes crude glycerol at about 1% w/v, corn steep liquor at about 2% w/v, yeast autolysate at about 0.5% w/v, wherein the growth medium has a pH of about 5.5. In some embodiments, growth conditions (oil production conditions) are provided for *P. kudriavzevii* using inexpensive raw materials such as corn steep liquor, crude glycerol and de-oiled yeast autolysate.

In some embodiments, the growth conditions (oil producing condition) for oleaginous yeast are performed to accommodate large scale fermentation and/or high density fermentation. In some embodiments, oil production is done at a smaller scale volume (e.g., 5 liters, "L"); in other embodiments, oil production is done at a larger scale volume (e.g., 27 L or more). In some embodiments, oil production is performed in a smaller fermentation volume and the parameters are then scaled-up for use in a larger volume fermentor. In some embodiments, the nutritional and physiological parameters are additionally provided in the larger volume fermentor after scale-up from the small volume. In some embodiments, inexpensive raw materials such as corn steep liquor and crude glycerol are used. In some embodiments, the oleaginous yeast is *P. kudriavzevii*, such as the yeast strain deposited under Accession No. MTCC 5493.

In some embodiments, methods are provided to allow oleaginous yeast production to high density in fermentors, using inexpensive raw materials including crude glycerol and corn steep liquor. In some embodiments, the oleaginous yeast is *P. kudriavzevii*, such as the yeast strain deposited under Accession No. MTCC 5493.

In some embodiments, methods are provided for oil extraction from oleaginous yeast. In some embodiments, oleaginous yeast is fermented under oil producing conditions, and oil is extracted from the fermented cells. In some embodiments, extraction includes lysing the fermented yeast cells (e.g., by homogenization or freezing) and extracting the oil using a polar organic solvent. By way of example, but not by way of limitation, polar organic solvents include chloroform and hexane. In some embodiments, the growth medium for fermentation includes inexpensive raw materials such as raw glycerol and corn steep liquor. In some embodiments, fermentation is performed to high density in a large volume (e.g., 27 L or greater). Thus, in some embodiments, methods are provided for oil extraction from oleaginous yeast which is cost effective, commercially viable and feasible on a large scale. In some embodiments, the oleaginous yeast is *P. kudriavzevii*, such as the yeast strain deposited under Accession No. MTCC 5493.

In some embodiments, methods are provided for the production of biodiesel (e.g., biodiesel comprising fatty acid methy esters, "FAMEs") from oleaginous yeasts. In some embodiments, methods are provided for biodiesel production using oil extracted from the newly isolated yeast *P. kudriavzevii* deposited under Accession No. MTCC 5493. In some embodiments, the methods include transesterification of oil extracted from the oleaginous yeast. In other embodiments, the methods include the direct transesterification of oleaginous yeast biomass to make biodiesel.

In some embodiments, methods are provided for oil extraction and biodiesel production from oleaginous'yeast, such as *Pichia kudriavzevii*, which is cost effective, commercially viable and feasible on a large scale.

In some embodiments, methods and compositions are provided to screen and isolate new strains of yeast able to accumulate oil.

In some embodiments, methods and compositions are provided to demonstrate biodiesel production using oil extracted from the newly isolated yeast *Pichia kudriavzevii* MTCC 5493

In some embodiments, methods and compositions are provided to optimize the physiological and nutritional parameters for improved production of yeast biomass by the one-variable-at-a-time method.

In some embodiments, methods and compositions are provided to optimize yeast production in high density in fermentor using cheap raw materials including crude glycerol and corn steep liquor.

In some embodiments, methods and compositions are provided to provide a process for extraction of oil from fermented yeast and transesterify the yeast to produce biodiesel.

In some embodiments, methods and compositions are provided, to provide a process for the direct transesterification of the yeast biomass to make biodiesel.

In some embodiments, methods and compositions are provided to provide a process, for producing biodiesel from yeast which is cost effective, commercially viable and feasible on a large scale.

In some embodiments, methods and compositions are provided to maximize the production of yeast in high density in fermentors using cheap raw materials including crude glycerol and corn steep liquor.

In some embodiments, methods and compositions are provided to screen and isolate new strain of yeast capable of accumulating oil. In one embodiment the present invention describes the identification of a new oil accumulating strain, *Pichia kudriavzevii* MTCC 5493 as characterized by its gene sequence analysis.

In some embodiments, methods and compositions are provided to optimize the nutritional and physiological parameters using the one variable at a time method. In some embodiments, such methods are used to improve the yields of yeast biomass. In some embodiments, methods and compositions are provided for batch and fed batch fermentation of yeast. In some embodiments, such methods include producing yeast biomass using crude glycerol and corn steep liquor. In one embodiment yeast are fermented in a large scale fermentor of up to 25 L scale.

In some embodiments, methods and compositions are provided to extract of oil from yeast.

In some embodiments, methods and compositions are provided for the transesterification of the yeast oil.

In some embodiments, methods and compositions are provided for the direct transesterification of the yeast biomass to make biodiesel.

IV. Examples

The following examples are included to demonstrate embodiments of the invention. It should be appreciated by those of skill in the art that the techniques disclosed in the examples which follow represent techniques discovered by the inventor to function well in the practice of the invention. However, those of skill in the art will, in light of the present disclosure, appreciate that many changes can be made in the specific embodiments that are disclosed and still obtain a like or similar result without departing from the spirit and scope of the invention.

Example 1

Screening and Isolation of Oleaginous Yeast

Eight different rotten fruit samples (mango, guava, orange, pomegranate, grapes, banana, papaya and chikku) were screened for oleaginous yeasts. Fruit samples were collected from the fruit market of Ghansoli, Navi Mumbai, India. Skins of the fruits were peeled and added to 100 ml of glucose-enriched medium containing (in g/L): glucose 10, peptone 5, yeast extract 5, malt extract 3, $KH_2PO_4$ 1 and $MgSO_4 \cdot 7H_2O$ 0.5, in a 250 ml Erlenmeyer flask. The samples were incubated in an incubator shaker at 28° C. for 48 h with shaking at 200 rpm, to enrich for yeast.

Example 2

Yeast Isolation

The enriched cultures were then serially diluted with sterile distilled water and 0.1 ml aliquots of the dilutions ranging from $10^{-6}$ to $10^{-12}$ were plated onto MGYP agar plates (1% glucose, 0.5% peptone, 0.5% yeast extract, 0.3% malt extract, 2% agar, and streptomycin (0.2 g/L)). The plates were incubated at 28° C. for 72 h, and isolated colonies with the morphology typical of yeasts were used for further study. About 250 of the isolated strains were further screened for the accumulation of lipid by a solvent extraction method (Folch et al., 1997), and one strain was found to be highly effective in accumulating oil as the other strains isolated produced negligible amount of oil (not measurable. For yeasts, the lipid accumulation process requires the exhaustion of a nutrient, usually nitrogen, to allow excess carbon to be incorporated into lipids. Thus further optimization was carried out on this strain for increase biomass and oil production.

Example 3

Identification of Yeast Strain

The yeast strain highly effective in accumulating oil, as discussed in Example 2 was identified as *Pichia kudriavzevii* strain on the basis of sequencing the D1/D2 domain of the 26S ribosomal RNA gene by the Microbial Type Culture Collection, Chandigarh, and given Accession No. 5493.

The strain was isolated by the inventors and deposited for the first time and given the accession number MTCC 5493.

Example 4

Growth and Maintenance of the Microorganism

The yeast strain *Pichia kudriavzevii* MTCC 5493, used in the experiments discussed below in Example 5, was grown in 250 ml flasks containing 100 ml of the MGYP medium containing (g/L): glucose 10; peptone 50; yeast extract 5; $K_2HPO_4$ 3; and $KH_2PO_4$ 1; pH 5.5. The medium was sterilized for 20 min at 121° C. and was inoculated with 2% seed inoculum (2 ml) and incubated at 30±1° C. for 24 h at 200 rpm.

Seed inoculum was cultured as above.

Example 5

Improved Biomass Production

The examples below identify a critical balance of different substrates and cultivation modes that achieve a high-density cell culture for microbial lipid fermentation.

A. Selection of Physico-Chemical Factors for Improvement of Yeast Biomass

Experiments were carried out by a method assaying, one at a time, various physico-chemical parameters or variables for the growth of *Pichia* yeast cells (*Pichia kudriavzevii*, MTCC Accession No. 5493). pH, inoculum density, and inoculum size were examined as physical parameters, while different carbon and nitrogen sources (organic and inorganic) were examined as nutritional parameters. The selected sources of carbon, nitrogen and salts were further investigated to arrive at certain concentrations for improved production of yeast cells (biomass). In each of the experiments described in Example 5, seed inoculum and the experimental batches of cells were grown as described in Example 4 unless otherwise stated.

B. Determination of Yeast Dry Mass

For the experiments described in Examples 5-12, the dry weight of yeast cell biomass was determined as follows. One ml of culture was centrifuged at 10,000 rpm for 10 min. The biomass pellet was washed twice with distilled water and dried at 40° C. to constant mass (usually 24 h). The biomass was determined gravimetrically.

C. Effect of Inoculum Density

Inoculum density ranging from 1 to 5% (v/v) and its effect on yeast biomass production was evaluated. FIG. 1 shows that inoculum density did not significantly affect the growth of the yeast strain and hence in all subsequent experiments 1% (v/v) inoculum was used.

D. Effect of pH on Yeast Biomass

Figure 2:
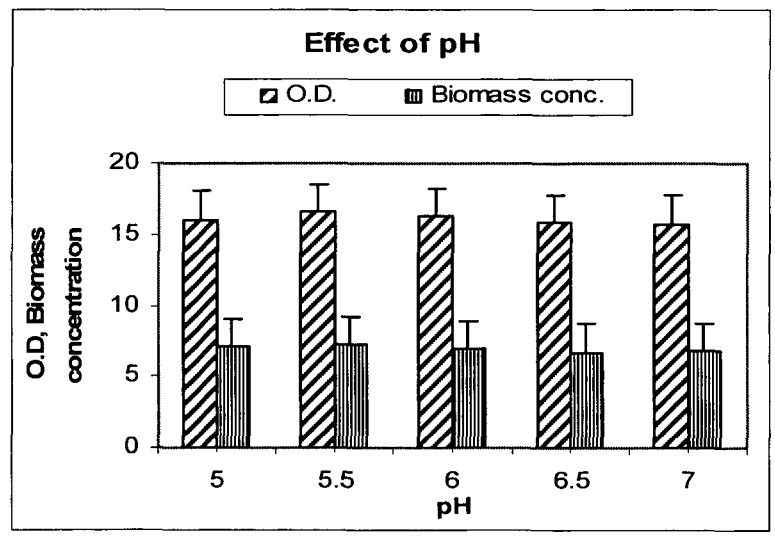
FIG. 2 shows the effect of pH of the medium on biomass production for *Pichia kudriavzevii*.

The effect of initial pH on yeast biomass production was studied, wherein the initial pH was varied from 5.0 to 7.0. A maximum optical density of 16.86 (dry weight of yeast cell biomass of 7.2 g/L) was obtained when the fermentation was carried out at pH 5.5 (FIG. 2).

E. Effect of Inoculum Age

Figure 3:
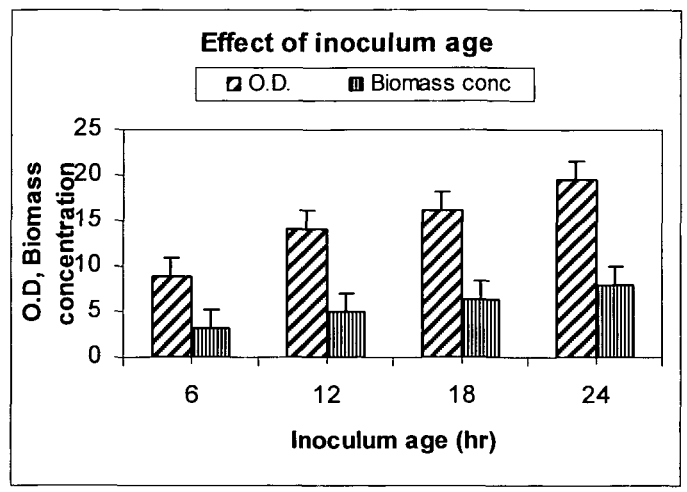
FIG. 3 shows the effect of inoculum age on biomass production for *Pichia kudriavzevii*.

Inoculum grown for varying time periods ranging from 6 h to 24 h was used to determine the effect of inoculum age on yeast biomass. A 24 h old inoculum seemed to give maximum OD of 19.6 with dry weight of yeast cell biomass of 8.1 g/L (FIG. 3)

F. Effect of Different Carbon Sources

Figure 4:
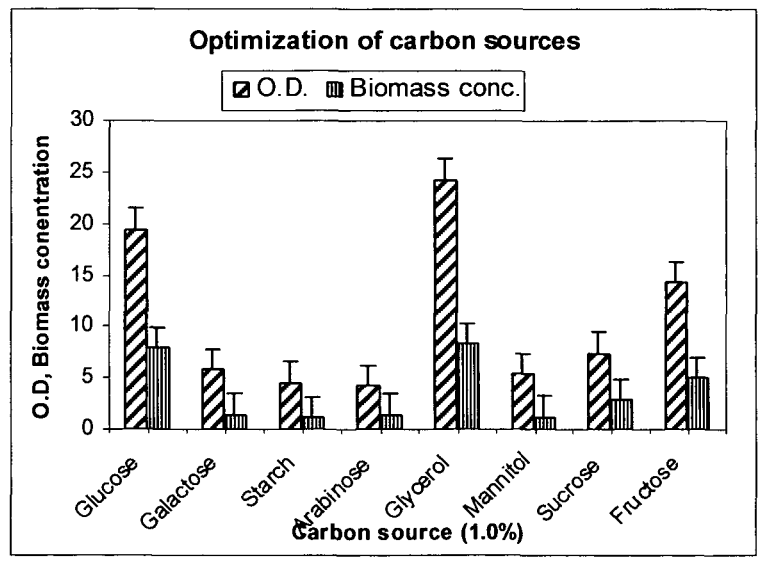
FIG. 4 shows the effect of carbon source on biomass production for *Pichia kudriavzevii*.
Figure 5:
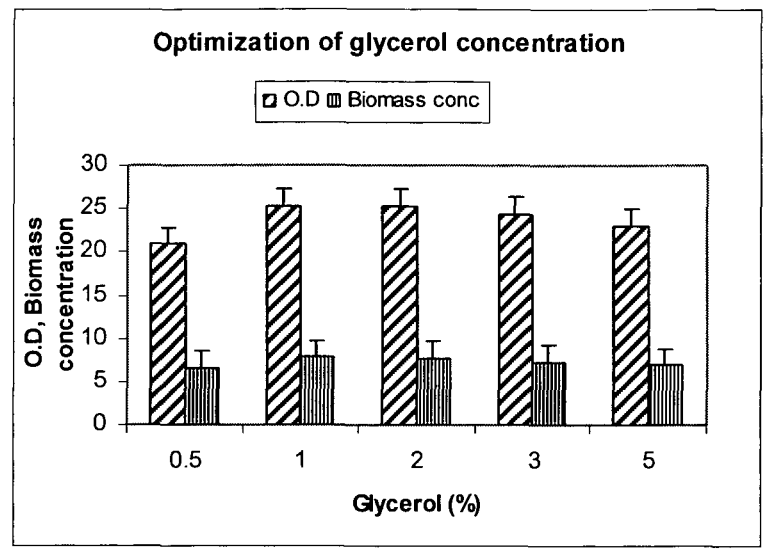
FIG. 5 shows the effect of glycerol concentration on biomass production for *Pichia kudriavzevii*.

Carbon source plays a role in both biomass and lipid production. The effect of various carbon sources including glucose, galactose, starch, arabinose, glycerol, mannitol, sucrose and fructose on biomass production was evaluated. Of all the carbon sources tested, glycerol was the best carbon source (FIG. 4) resulting an O.D. of 25.35 and dry weight of yeast cell biomass of 8.3 g/L. Further optimization related to the concentration of glycerol in the medium showed that the highest optical density of 25.25 with a dry cell weight of 7.8 g/L was obtained at a glycerol concentration of 1% (FIG. 5).

G. Effect of Different Nitrogen Sources

Figure 6:
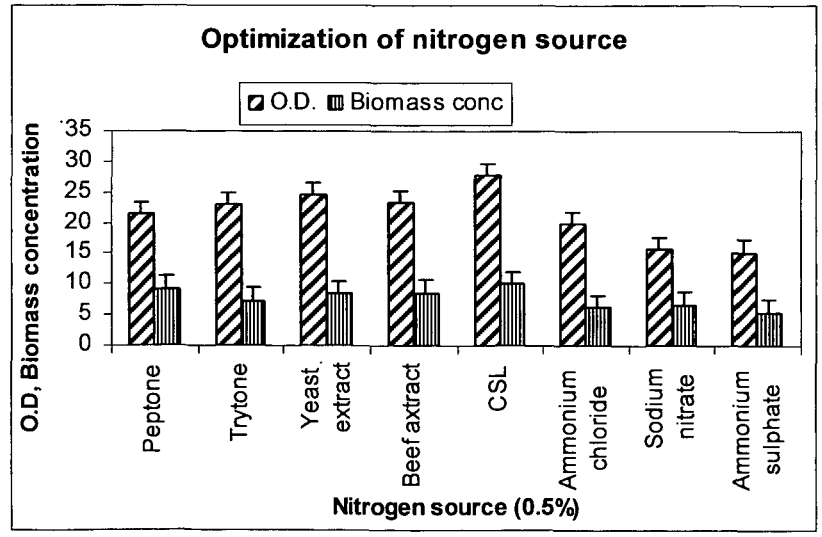
FIG. 6 shows the effect of nitrogen source on biomass production for *Pichia kudriavzevii*.
Figure 7:
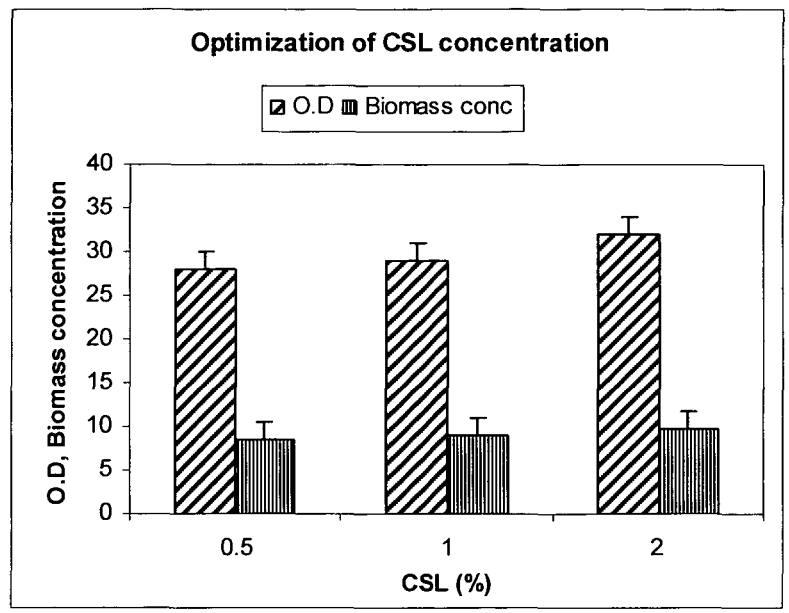
FIG. 7 shows the effect of corn steep liquor concentration on biomass production for *Pichia kudriavzevii*.

The nitrogen source in the medium was replaced with various organic and inorganic nitrogen sources including peptone, tryptone, yeast extract, beef extract, corn steep liquor, ammonium chloride, sodium nitrate and ammonium sulphate. Corn steep liquor ("CSL") was found to be the best nitrogen source (FIG. 6). An evaluation of CSL concentration shows that the OD is boosted to 31.92 with a dry cell weight of 9.85 g/L (FIG. 7) at 2% CSL.

Example 6

Scale-Up Studies in a 7 L Fermentor

The scale-up of the production of yeast cells (*Pichia kudriavzevii*, MTCC Accession No. 5493) was carried out in a bioreactor (Sartorius B-plus, Germany) with a working volume of 5.0 liters ("L"). Scale-ups were performed as described in sections A-C, below.

A. Determination of Oil Yield

For the experiments described in Examples 7-12, oil yield from the fermented yeast cells was determined by dividing the quantity of oil by dry cell weight of cells taken for oil extraction.

B. Batch and Fed Batch Fermentation Using MGYP Medium

Figure 8:
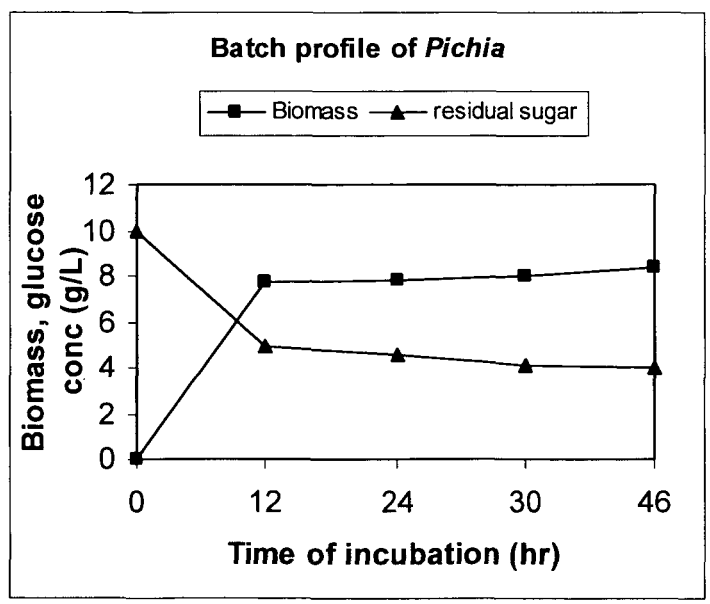
FIG. 8 shows the batch fermentation profile for the production of *Pichia kudriavzevii* biomass.
Figure 9:
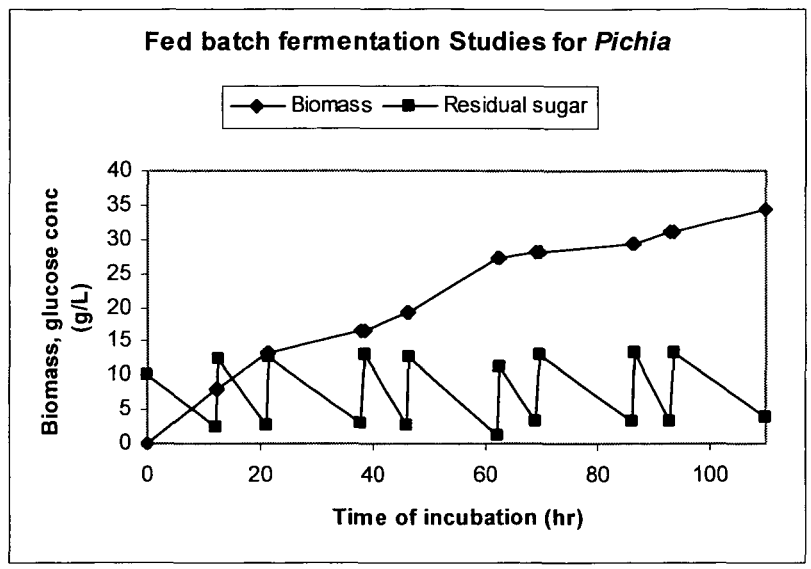
FIG. 9 shows the fed batch fermentation profile for the production of *Pichia kudriavzevii* biomass.

To promote high density growth, *Pichia krudriavzevii* cells (MTCC 5493) were grown in MGYP medium containing peptone, yeast extract, malt extract and glucose. Cells were grown in a fermentor in either batch or fed batch mode. The fermentation was carried out at pH 5.5. pH was maintained during the run by adding liquid ammonia as necessary. The agitation was kept at 350 rpm with 3 win of aeration. For batch fermentation, the run was carried out for 48 h at 28° C. resulting in an O.D. of 24.2 in 48 h with dry weight of yeast cell biomass of 8.4 g/L (FIG. 8). Thereafter, there was a decline in the biomass production. To improve the yeast cell density, fed batch fermentation was attempted. The fermentor was run for 120 h under the conditions used for batch mode, except 1% glucose was added to the fermentor as feed when glucose levels dropped to below 5 g/L. Results shown in FIG. 9 indicate that a maximum dry weight of biomass of 34.5 g/L was obtained in 110 h. The O.D. was 101.35. Oil extraction was not done.

Figure 10:
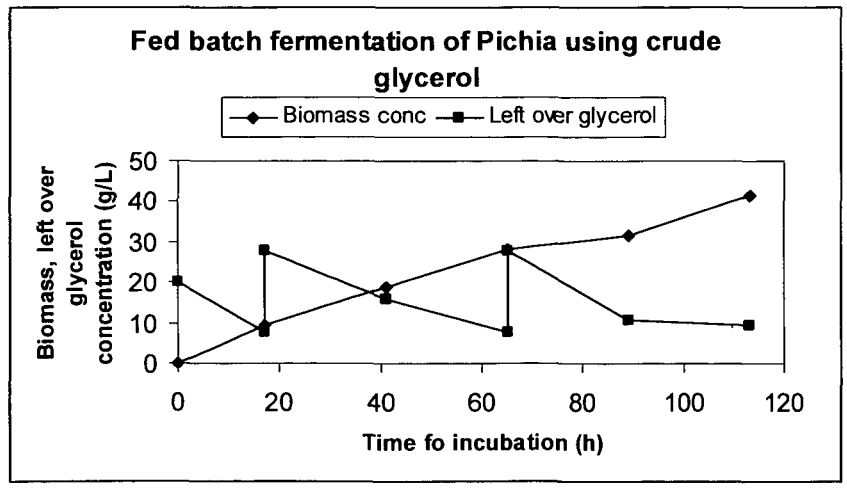
FIG. 10 shows the fed batch fermentation profile for the production of *Pichia kudriavzevii* using low cost medium.

C. Fed Batch Fermentation Using Low Cost Substrate, Such as Crude Glycerol and CSL To bring down the cost of the fermentation medium, peptone and yeast extract were replaced with corn steep liquor ("CSL"), a cheap raw material, and glucose was replaced with crude glycerol. Glycerol and CSL were identified in the Example 5. The fermentor medium was made up of crude glycerol 2%; CSL 1% and malt extract 0.2%. The fermentation was run for 120 h at 28° C. and a pH of 5.5. The agitation was at 350 rpm with 3 vvm of aeration. Crude glycerol (2%) was added as feed in the fermentor after 17 h and 65 h of incubation, when the glycerol concentration was reduced below 8 g/L. Glycerol levels were brought up to 30 g/L. The results show that a biomass of 42 g/L was obtained in 112 h of incubation (FIG. 10); the O.D. at 112 h was 106.

Example 7

Figure 11:
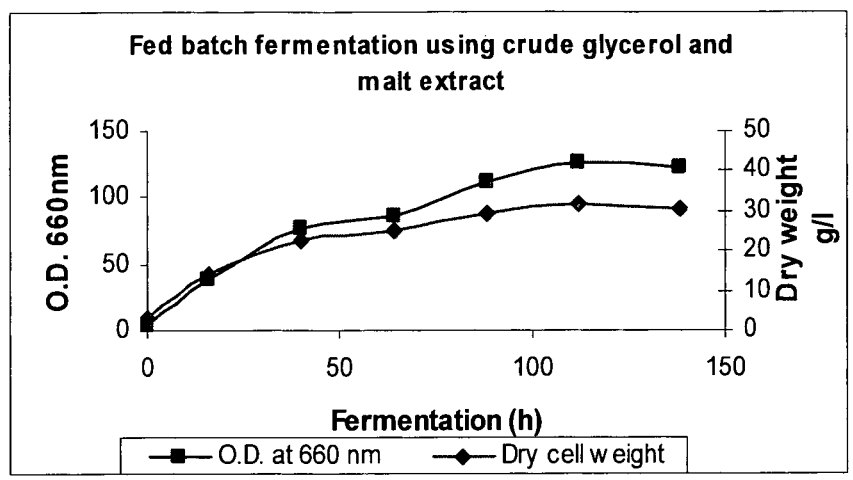
FIG. 11 shows the high cell density fermentation using crude glycerol derived from biodiesel industry

High Cell Density Fermentation Using Crude Glycerol Derived from Biodiesel Industry Fed batch fermentation was carried out in a bioreactor (Sartorius C-plus, Germany) with a working volume of 5.0 L. To promote high density growth, *Pichia kudriavzevii* cells (MTCC 5493) were grown in medium containing crude glycerol 1% w/v; corn steep liquor 2% w/v, baker's yeast 0.5% w/v and malt extract 0.2% w/v. The medium was inoculated with 20% v/v inoculum prepared as described in Example 4, above. The fermentor was run in fed batch mode at pH 5.5. pH was controlled during the run by adding 3 N sodium hydroxide and/or 3 N sulphuric acid as necessary. The fermentation parameters were agitation at 700 rpm with 1 vvm of aeration. In total, 6% v/v glycerol was added to the fermentor as feed added from a concentrated stock solution of glycerol so that final concentration is 1% during every feed during the course of fermentation when glycerol levels dropped to below 8 g/L. Results shown in FIG. 11 indicate that a maximum O.D. of 123 and dry weight of biomass of 30.4 g/l was obtained in 138 h of fermentation with an oil yield of 13.76%, the oil extraction process was optimized subsequently) on a dry weight basis.

Example 8

Fed Batch Fermentation without Malt Extract

Figure 12:
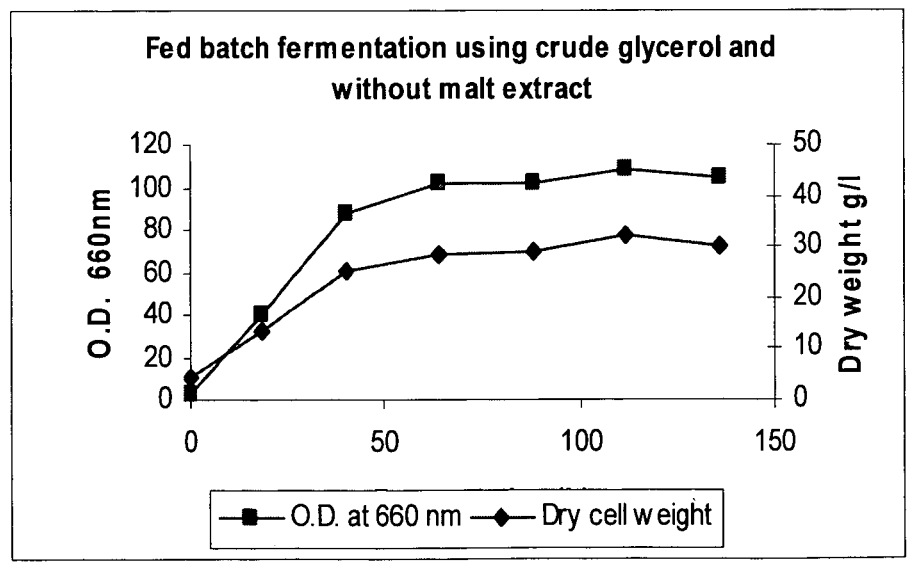
FIG. 12 shows the fed batch fermentation without malt extract

In order to reduce medium cost, fed batch fermentation was carried out excluding malt extract in the medium. All other fermentation parameters were kept constant (the same as described in Example 7). The fermentor was run for 136 hr and 6% v/v glycerol was added to the fermentor as feed when glycerol levels dropped to below 8 g/L. Feed was added from a concentrated stock solution of glycerol so that final concentration is 1% during every feed. Results shown in FIG. 12 indicate that a maximum O.D. of 104 was obtained in 136 h with a dry weight of yeast cell biomass of 30.1 g/L. The oil yield was 21% on dry weight basis. Thus, malt extract could be eliminated from the medium without compromising biomass yield.

Example 9

Scale Up of Fed Batch Fermentation without Malt Extract at 27 L Level

Figure 13:
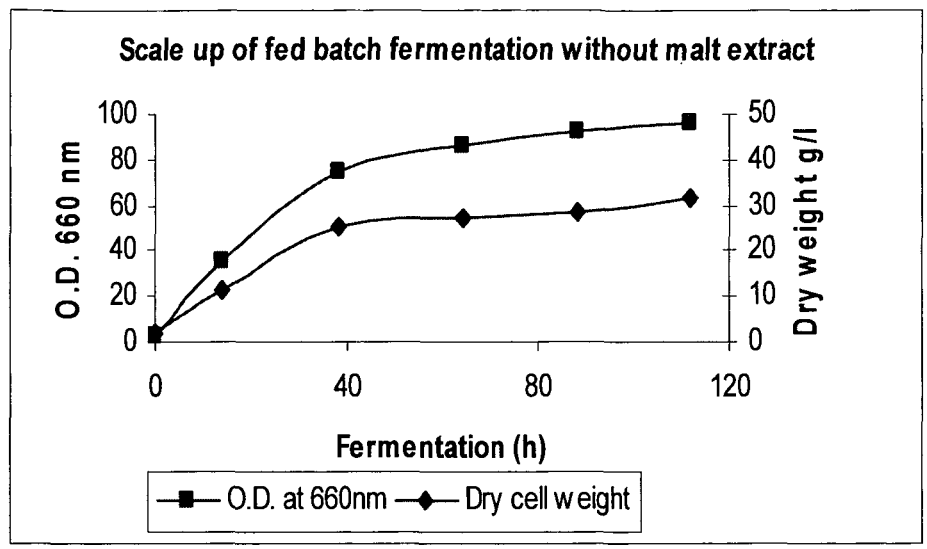
FIG. 13 depicts the profile during scale-up of fed batch fermentation without malt extract at 27 L level.

Fed batch fermentation described in Example 8 was scaled up to 27 L in a Bioflow-5000 fermentor (New Brunswick). All other fermentation parameters were kept constant except the agitation was carried out at 350 rpm per tip speed of the impeller. The fermentor was run for 112 h and 6% v/v glycerol was added in the fermentor as feed when glycerol levels dropped to below 8 g/L. as described in Example 8. Results shown in FIG. 13 indicate that a maximum O.D. of 96.36 was obtained in 112 h with dry weight of yeast cell biomass of 31.8 g/L. Oil yield was determined to be 22% on dry weight basis.

Example 10

Fed Batch Fermentation Using De-Oiled *Cryptococcus* Yeast as a Nitrogen Source

Figure 14:
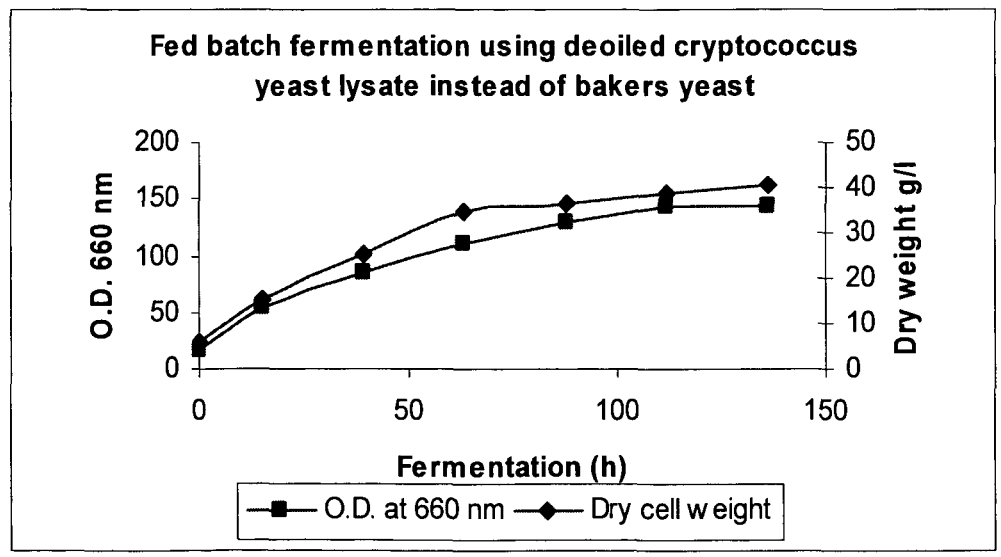
FIG. 14 shows the fed batch fermentation using de-oiled *Cryptococcus* yeast as a nitrogen source.

To make the process more economically viable, baker's yeast autolysate in the medium was replaced by de-oiled *Cryptococcus curvatus* yeast cells collected from other fermentations. All other media components and fermentation conditions were the same as described in Example 8 The fermentor medium constituted crude glycerol 1% w/v; CSL 2% w/v and *Cryptococcus* yeast autolysate 0.5% w/v. The fermentation was carried out at 28° C. and a pH of 5.5. The fermentor was run for 136 h and 7.5% v/v glycerol was added in the fermentor as feed when the glycerol levels dropped to below 8 g/L as described in Example 8. Results shown in FIG. 14 indicate that a maximum O.D. 144 was obtained in 136 h with the dry weight of yeast cell biomass of 40.6 g/L. The oil yield was determined to be 14.8% on dry weight basis.

Example 11

Fed Batch Fermentation Using Seed and Production Media with Same Composition

In all the previous batches, the seed inoculum was always grown in MGYP medium, as described in Example 4. However, biodiesel is a commodity product that should have competitive pricing; accordingly, every bit of economization is warranted. Therefore, the seed inoculum was grown in the same low-cost medium as that used in production which constituted crude glycerol 1% w/v; CSL 2% w/v and *Cryptococcus* yeast autolysate 0.5% w/v.

The medium for fed batch fermentation was inoculated with 20% v/v seed inoculum and the fermentation was carried out at 28° C. and a pH of 5.5. All other parameters were the same as described in Example 10, except that the fermentor was run for 114 h and 4.5% v/v glycerol was added in the fermentor as feed when glycerol levels dropped below 8 g/L.

Figure 15:
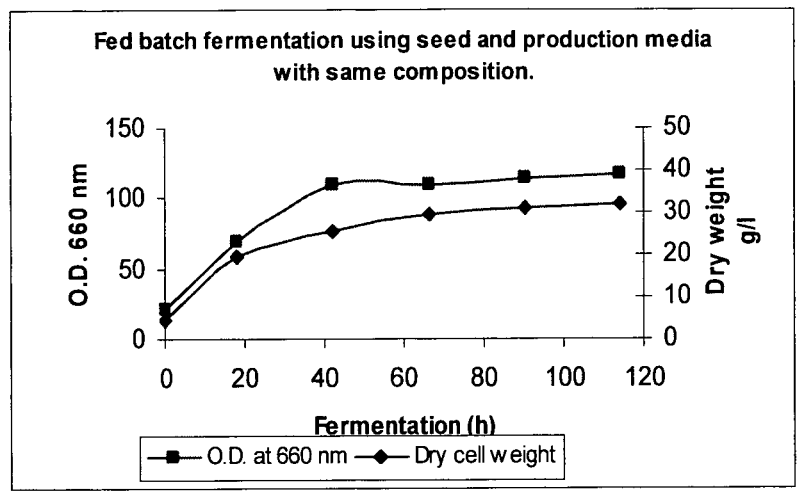
FIG. 15 depicts the fed batch fermentation using seed and production media with same composition.

Feed was added from a concentrated stock solution of glycerol so that final concentration is 1% during every feed. Results shown in FIG. 15 indicate that a maximum O.D. of 116.5 was obtained in 114 h with dry weight of yeast cell biomass of 31.8 g/L. The oil yield was 20.16% on dry weight basis. The amount of glycerol feed is reduced to ensure complete utilization of glycerol and elimination of any residual glycerol at the end of fermentation.

Example 12

Figure 16:
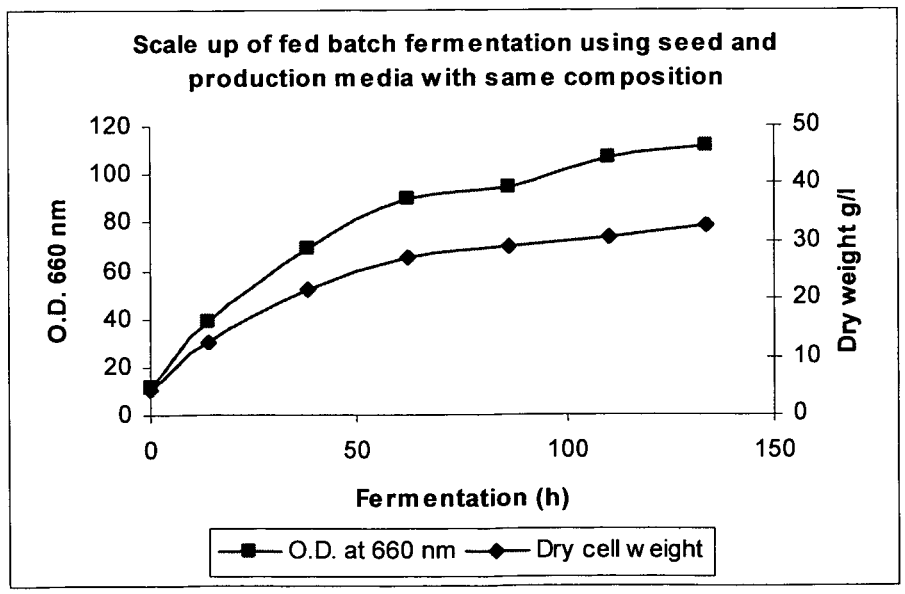
FIG. 16 shows the scale-up of fed batch fermentation using seed and production media with same composition.

Scale-Up of Fed Batch Fermentation Using Seed and Production Media with Same Composition Scale-up of fed batch fermentation described in Example 11 was performed at the 27 L scale. Both the fermentor medium and seed medium constituted crude glycerol 1% w/v; CSL w/v and *Cryptococcus* yeast autolysate 0.5% w/v. Seed inoculum was added to the fed batch fermentation medium at 20% v/v, and the fermentation was carried out at 28° C. and at pH of 5.5. Other parameters were the same as described in Example 11, except the scale of the fermentation (5 L vs. 27 L) and the fermentor, a Bioflow-5000 fermentor from New Brunswick was used in this Example. The fermentor was run for 134 h and 4.5% v/v glycerol was added in the fermentor as feed when glycerol levels dropped below 8 g/L. Feed was added from a concentrated stock solution of glycerol so that final concentration is 1% during every feed. Results shown in FIG. 16 indicate that a maximum O.D. of 111.6 was obtained in 134 h with a dry weight of yeast cell biomass of 32.8 g/L. The oil yield was calculated to be 21.5% on a dry weight basis.

Example 13

Oil Extraction from Yeast Cells (Folch's Oil Extraction Method)

The yeast biomass produced by a fermentation method as described in any of the above examples is homogenized with 20 volumes of chloroform:methanol (2:1) mixture (1 g in 20 ml of solvent mixture). After dispersion, the whole mixture is agitated overnight in an orbital shaker at room temperature. The homogenate is centrifuged to recover the liquid phase. The solvent is washed with 0.2 volumes (4 ml for 20 ml) of water or 5% sodium sulphate/NaCl solution. After vortexing for few seconds, the mixture is centrifuged at low speed (2000 rpm) to separate the two phases. After removal of the upper phase by siphoning, the lower chloroform phase containing lipids is evaporated under vacuum in a rotary evaporator or under a nitrogen stream if the volume is under 2-3 ml.

Alternatively, the extraction of oil from yeast biomass can be done using n-hexane-isopropyl alcohol. A 3:2 ratio of n-hexane:IPA was used. In a typical batch, 50 grams (dry cell weight) of cells were mixed with 5.4 L n-hexane and 3.6 L IPA and stirred overnight at room temperature. To completely separate the n-hexane layer, 1 L of water was added to the mixture and stirred. The n-hexane layer was recovered and evaporated in a rotavapor to recover oil.

Example 14

Trans Esterification of the Oil Extracted from Yeast

For biodiesel production, the oil extracted from *Pichia kudriavzevii*, MTCC Deposit No. 5493, as described above in Example 13, was subjected to transesterification. Typically, 0.8 ml of methanol was added to 10 g of oil and thoroughly mixed at 150 rpm for 1 h. The mixture was acidified with $H_2SO_4$ (0.1%) and the acidification reaction reaction was carried out at 35° C., 150 rpm for 1 h. NaOH (0.4%) dissolved in methanol was added to the reaction mixture slowly with constant stirring. The reaction mixture was held at 70° C. for 1 h with constant stirring at 150 rpm. The reaction mixture was then set aside for phase separation; the upper phase containing FAMEs (biodiesel) was removed and analyzed.

Example 15

Extraction of Fame from Yeast Cells by Direct Transesterification

FAMEs were extracted by direct transesterification per the procedure of Lee et al. In brief, freeze dried cells (1 g)

fermented as described in any of the above examples, were added to a mixture of 10 ml of methanolic sulphuric acid (0.1% sulphuric acid in methanol) and mixed vigorously. 10 ml of chloroform was added and the mixture was heated at 80° C. for 2 h. A synthetic antioxidant (propyl gallate) was added to the mixture during transesterification, and then the mixture was cooled. 20 ml of water was then added to the mixture and shaken vigorously. After leaving the mixture for phase separation (12 h), FAMEs were recovered from the chloroform extract.

Example 16

Homogenization of the Fermentation Broth and Oil Extraction

To eliminate the step of centrifugation for collecting cell mass, a direct homogenization of the fermented broth was performed. The fermented broth was subjected to homogenization at 4° C. under 800 bars of pressure in a homogenizer to break the cells. The duration for passage of 1 L of cells is 4 min. Five passages were taken to break the cells. Homogenized cells were mixed with hexane (1:2 ratio or homogenized cells:hexane) to extract the oil. The extraction process was carried out in 50 L agitator tank for 1 h at 950 rpm. After phase separation, the aqueous layer was removed and isopropyl alcohol ("IPA") was added to the hexane layer which was concentrated to recover the oil.

Example 17

Analysis of FAME by GC

The FAME esters extracted as described in Example 16 were analyzed by gas chromatography (Agilent series) that was equipped with flame ionization detector. The analysis was done on a Supelco omega wax 250 fused capillary silica column (30 m×0.25 m). The oven time-temperature profile is: 140° C. (initial), 4° C. per min to 240° C., 240° C. (10 min), with a total run time of 30 min. The identification and quantification of the FAME was done using each FAME's respective standard (Sigma).

Example 18

Comparative Analysis of Lipids

The fatty acid content of oil extracted from *Pichia kudriavzevii* (MTCC 5493) as described in Example 17 was compared with that of *C. curvatus* oil and Jatropha oil.

Oil extraction of *Cryptococcus curvatus* was carried out by using n-hexane:IPA at a ratio of 3:2. Centrifuged wet cells (500 g) were mixed with 9 L of n-hexane:IPA (3:2) and stirred overnight room temperature. Water (1 L) was added to the mixture to separate the n-hexane layer completely which occurs immediately on agitation. Oil was recovered from the n-hexane layer by evaporation of the solvent in the rotavapor. Jatropha oil was obtained by extracting crushed jatropha curcas seeds with petroleum ether in a Soxhlet apparatus. The oil in the seeds get extracted in the solvent which is then evaporated in a rotavapor to obtain the oil.

The fatty acid profile of both *P. kudriavzevii* and *C. curvatus* (Table 1) were comparable to that of Jatropha oil suggesting the suitability of the yeast oil for the production of biodiesel. This is the first time a *Pichia* strain has been shown to be accumulating oil (oleogenic). In general, the genus *Pichia* are considered as the workhorse for molecular genetic techniques in yeast and has been extensively studied. Therefore, future manipulation of *Pichia* strain for improved oil production would be a much easier task due to the knowledge and ease of manipulation of this strain of yeast. The oil composition of *Pichia* consisted of all the known fatty acids present in Jatropha oil which is well known source for producing biodiesel. Therefore, oil from *Pichia* is also considered suitable for biodiesel production.

TABLE 1

Comparative analysis of oil samples

| Type of fatty acid | Jatropha oil | Cryptococcus oil | Pichia kudriavzevii oil |
|---|---|---|---|
| C14:0 (Myristic acid) | — | 02.43% | — |
| C16:0 (Palmitic acid) | 14.66% | 34.48% | 10.89% |
| C16:1(Palmitoleic acid) | 0.94% | 01.47% | 8.22% |
| C18:0 (Stearic acid) | 6.86% | 6.84% | 1.80% |
| C18:1 (Oleic acid) | 39.08% | 38.98% | 41.36% |
| C18:2 (Linoleic acid) | 32.48% | 07.62% | 15.88% |
| C18:3 (Linolenic acid) | 0.30% | 00.84% | 6.65% |
| C20:0 (Arachidic acid) | 0.24% | 0.85% | — |
| UNKNOWN | 5.44% | 6.1% | 15.20% |

Thus, the present disclosure describes a simple fed-batch process for lipid production by oleaginous yeast *Pichia kudriavzevii*, such as that deposited under Accession No MTCC 5493. The process features a low cost medium, containing crude glycerol and CSL. The use of these industrial byproducts increased biomass and lipid productivity while reducing costs of production.

Thus, while we have described fundamental novel features of the invention, it will be understood that various omissions and substitutions and changes in the form and details may be possible without departing from the spirit of the invention. For example, it is expressly intended that all combinations of those elements and/or method steps, which perform substantially the same function in substantially the same way to achieve the same results, be within the scope of the invention.

The invention claimed is:

1. A composition comprising oil produced by the isolated yeast cell of *Pichia kudriavzevii*, deposited or identified as MTCC Accession No. 5493, wherein the isolated yeast cell is able to accumulate at least about 50% oil on a dry weight basis under oil production conditions, wherein the oil production conditions comprise growing the cell in a culture medium comprising crude glycerol, corn steep liquor and yeast autolysate, the medium at a pH of about 5.5, wherein the composition is obtained by subjecting the oil after extraction to transesterification and wherein the oil comprises:
    at least about 10% palmitic acid,
    at least about 8% palmitoleic acid,
    at least about 1% stearic acid,
    at least about 41% oleic acid,
    at least about 15% linoleic acid, and
    at least about 6% linoleic acid.

2. A method for culturing the isolated yeast cells of a *Pichia kudriavzevii* strain, deposited or identified as Accession No. MTCC 5493, wherein the isolated yeast cells are able to accumulate at least about 10% oil on a dry weight basis under oil production conditions, wherein the oil production conditions comprise growing the cells in a culture medium comprising crude glycerol, corn steep liquor and yeast autolysate, the medium at a pH of about 5.5 to induce oil production by the cells, the method comprising:
  a) providing the culture medium comprising:
    the crude glycerol at about 1% w/v, the corn steep liquor at about 2% w/v, the yeast autolysate at about 0.5% w/v; and
  b) fermenting the yeast cells in the culture medium using fed batch fermentation at about 28° C. for at least about 100 hours.

3. The method of claim 2, wherein the fermentation runs for at least about 110 hours.

4. The method of claim 2, wherein the fed batch fermentation comprises adding glycerol during the fermentation.

5. The method of claim 4, wherein the added glycerol comprises crude glycerol.

6. The method of claim 4, wherein glycerol is added to the culture medium when the glycerol concentration of the fermentation is below about 8 g/L.

7. The method of claim 2, wherein fermentation continues until the O.D. of the yeast cells is between about 110 and 150.

8. The method of claim 2, wherein the fermentation results in an oil yield of at least about 14% on a dry weight basis.

9. The method of claim 2, wherein the fermentation results in an oil yield of at least about 20% on a dry weight basis.

10. The method of claim 2, wherein fermented cell biomass after fermentation is at least about 30 g/L on a dry weight basis.

11. A method for producing oil comprising fatty acid methyl esters, the method comprising:
  a) culturing the isolated yeast cell of *Pichia kudriavzevii*, deposited or identified as MTCC Accession No. 5493, wherein the isolated yeast cell is able to accumulate at least about 10% oil on a dry weight basis under oil production conditions, wherein the oil production conditions comprise growing the cell in a culture medium comprising crude glycerol, corn steep liquor and yeast autolysate, the medium at a pH of about 5.5;
  b) extracting the oil from the cultured yeast cells.

12. The method of claim 11, further comprising transesterifying the extracted oil.

13. The method of claim 11, wherein culturing under the oil production conditions comprises:
  a) providing the culture medium comprising:
    the crude glycerol at about 1% w/v, the corn steep liquor at about 2% w/v, the yeast autolysate at about 0.5% w/v; and
  b) fermenting the yeast cell in the culture medium using fed batch fermentation at about 28° C. for at least about 100 hours.

14. A method for producing biodiesel comprising fatty acid methyl esters, the method comprising:
  a) culturing the isolated yeast cells of a *Pichia kudriavzevii* strain, deposited or identified as Accession No. MTCC 5493, wherein the isolated yeast cells are able to accumulate at least about 10% oil on a dry weight basis under oil production conditions, wherein the oil production conditions comprise growing the cells in a culture medium comprising crude glycerol, corn steep liquor and yeast autolysate, the medium at a pH of about 5.5;
  b) extracting oil from the cultured yeast cells; and
  c) transesterifying the extracted oil.

15. The method for producing biodiesel comprising fatty acid methyl esters as claimed in claim 14, the method comprising:
  a) culturing yeast cells comprising *Pichia kudriavzevii*, MTCC Accession No. 5493, under oil production-conditions, wherein the cultured yeast cells accumulate at least about 10% oil on a dry weight basis; and
  b) extracting fatty acid methyl esters by direct transesterification from the yeast cells.

16. The method for producing biodiesel comprising fatty acid methyl esters as claimed in claim 14, the method comprising:
  a) culturing the isolated yeast cell of *Pichia kudriavzevii*, deposited or identified as MTCC Accession No. 5493, wherein the isolated yeast cell is able to accumulate at least about 10% oil on a dry weight basis under oil production conditions, wherein the oil production conditions comprise growing the cell in a culture medium comprising crude glycerol, corn steep liquor and yeast autolysate, the medium at a pH of about 5.5; and
  b) extracting oil from the cultured yeast cells, wherein the oil comprises fatty acid methyl ester.

17. The isolated yeast cell of *Pichia kudriavzevii*, deposited or identified as MTCC Accession No. 5493, wherein the isolated yeast cell is able to accumulate at least about 50% oil on a dry weight basis under oil production conditions, wherein the oil production conditions comprise growing the cell in a culture medium comprising crude glycerol, corn steep liquor and yeast autolysate, the medium at a pH of about 5.5.

18. The isolated yeast cell of claim 17, wherein the culture medium comprises
  the crude glycerol at about 1% w/v,
  the corn steep liquor at about 2% w/v, and
  the yeast autolysate at about 0.5% w/v.

* * * * *